| United States Patent [19] | [11] Patent Number: 4,948,583 |
|---|---|
| Grollier et al. | [45] Date of Patent: Aug. 14, 1990 |

[54] COSMETIC COMPOSITION FOR THE TREATMENT OF HAIR, PARTICULARLY OILY HAIR, BASED ON AN EXTRACT OF YARROW (ACHILLEA MILLEFOLIUM L)

[75] Inventors: Jean-François Grollier, Paris; Georges Rosenbaum, Asnieres, both of France

[73] Assignee: Société Anonyme dite : L'Oreal, Paris, France

[21] Appl. No.: 342,672

[22] Filed: Apr. 21, 1989

[51] Int. Cl.$^5$ .......................... A61K 7/06; A61K 7/40; A61K 9/12; A61K 35/78

[52] U.S. Cl. .................................... 424/195.1; 424/47; 424/59; 424/60; 424/70; 424/71; 424/72; 424/78; 424/80; 514/864; 514/880; 514/881; 514/937; 514/944

[58] Field of Search ....................................... 424/195.1

[56] References Cited

U.S. PATENT DOCUMENTS

| 3,522,350 | 7/1970 | Goldberg et al. ................... 424/195 |
| 4,459,285 | 7/1984 | Grollier et al. ...................... 424/74 |
| 4,525,344 | 6/1985 | Tutsky .................................. 424/73 |
| 4,569,839 | 2/1986 | Grollier et al. ...................... 424/74 |
| 4,581,230 | 4/1986 | Grollier et al. ...................... 424/74 |

FOREIGN PATENT DOCUMENTS

| 3300491 | 7/1984 | Fed. Rep. of Germany . |
| 2067899 | 8/1981 | United Kingdom . |

OTHER PUBLICATIONS

Lewis et al., *Medical Botany*, pp. 338–339 (1977).

*Primary Examiner*—Dale R. Ore
*Attorney, Agent, or Firm*—Oliff & Berridge

[57] ABSTRACT

A cosmetic composition for the treatment of hair, in particular oily hair. The composition includes an appropriate carrier and a non-allergenic dry extract of yarrow (*Achillea millefolium* L), obtained by oxidation of a water-alcohol solution extract of flower tops of yarrow. The extract contains less than 0.5% by weight of polyphenolic derivatives.

1 Claim, No Drawings

COSMETIC COMPOSITION FOR THE TREATMENT OF HAIR, PARTICULARLY OILY HAIR, BASED ON AN EXTRACT OF YARROW (ACHILLEA MILLEFOLIUM L)

This is a continuation of application Ser. No. 07/120,744 filed Nov. 13, 1987 which in turn is a continuation of Ser. No. 06/854,519, filed Apr. 22, 1986 (now both abandoned).

BACKGROUND OF THE INVENTION

A. Field of the Invention

The present invention relates to a cosmetic composition for the treatment of hair, in particular oily hair, containing a dry extract of yarrow (Achillea millefolium L) obtained by oxidation of a water-alcohol extract of the flower tops of yarrow.

B. Description of the Prior Art

Different extracts of yarrow have been proposed for the treatment of hair. For example, French Patent No. 78,22837 describes the utilization of an extract of yarrow rich in polyphenolic derivatives of the flavonoid group in the manufacture of bleaching shampoos.

Preparation of the extract according to the invention must be carried out under conditions which do not lead to any degradation of polyphenolic derivatives, which are particularly sensitive to heat.

The essential oil of yarrow is a volatile oil which has been promoted by different authors in the field of cosmetics for the treatment of oily skin and for the treatment of hair seborrhea, the essential oil of yarrow possessing antiseptic and anti-inflammatory properties due to the relatively high percentage of azulene therein.

The essential oil of yarrow consists essentially of azulene, α- and β-pinene, caryophyllene, borneol, terpineol, cineole, bornyl acetate and other volatile components of diverse structures.

The utilization of extracts of yarrow, in particular water-alcohol extracts, up to now has given rise to certain difficulties. The extracts of yarrow have been found to possess a sensitizing action on certain subjects, thereby provoking allergic phenomena (see "Encyclopedia of common natural ingredients used in Food, Drugs and Cosmetics" by Albert Y. Leung, Wiley, 1980, p. 326).

After several studies on water-alcohol extracts of yarrow were completed, it was ascertained, surprisingly, that the allergenic properties could be reduced and even suppressed by submitting the water-alcohol extract solutions to an oxidizing treatment. Dry extracts of yarrow obtained after this treatment are devoid of sensitizing power but nevertheless retain the particular properties effective for the treatment of the oily appearance of hair, while also conferring softness and luster to the hair.

However, it was suspected that subjecting the water-alcohol extracts of yarrow to an oxidizing treatment, in order to eliminate the sensitizing power, would simultaneously provoke a deterioration of the active ingredients for the treatment of oily hair. However, tests have been carried out which prove that this activity is preserved and even enhanced.

The dry extracts of yarrow after oxidation are characterized by a very low content of polyphenolic derivatives and by the absence of polysaccharidic polymers and essential oil.

SUMMARY OF THE INVENTION

Accordingly, the object of the present invention is a cosmetic composition for treating hair, in particular oily hair, comprising an appropriate carrier and at least a non-allergenic dry extract from yarrow (Achillea millefolium L) obtained by oxidation of a water-alcohol extract solution of the flower tops of yarrow, and wherein the extract contains less than 0.5% by weight of polyphenolic derivatives.

DETAILED DESCRIPTION OF THE INVENTION

One typically assumes that the sensitizing properties of the dry extract of yarrow are associated with the polyphenolic derivatives (Flavonoids) that are present and which consist essentially of umbelliferone, luteolin and apigenin.

The percentage of polyphenolic derivatives in dry extract of yarrow before oxidation is about 5%, whereas after oxidation this percentage is less than 0.5% and even less than 0.3%.

The yarrow (Achillea millefolium L) is a herbaceous plant of the composite family (compositae-anthemidae), is perennial, has an aromatic odor and is 40 to 90 cm high with leaves highly divided into narrow segments (which gives the illusion that they are numerous, hence the name yarrow*) with white or sometimes pink flowers.

*The French name for yarrow, millefeuille, means thousand leaves.

The dry extract of yarrow utilized in the compositions according to the present invention is obtained from either fresh of dried flower tops in their raw state or eventually by previous grinding.

The procedure comprises making an infusion of the flower tops in water and filtering the aqueous solution after cooling. The solid residue is then dissolved in a lower aliphatic alcohol containing 1 to 3 carbon atoms, such as methanol, and after subsequent filtration the aqueous and alcoholic extracts are mixed, thereby yielding a turbid solution with a brown-greenish color.

The water-alcohol solution is then subjected to an oxidizing treatment with the aid, for example, of sodium hypochlorite at room temperature. After filtration, the dry extract is obtained by evaporation, atomization or freeze-drying.

The dry extract thereby obtained after treatment with sodium hypochlorite contains a certain proportion of sodium chloride which can be eliminated. However, it has been ascertained that the dry extract as obtained by the procedure described above may be utilized without any additional treatment in the compositions for the treatment of oily hair.

In the compositions according to the present invention the dry extract of yarrow, expressed as dry matter, is present at a concentration between 0.02 and 5% by weight, and preferably between 0.02 and 2% by weight with respect to the total weight of the composition.

The carriers for the compositions include water, an alcohol possessing 1 to 4 carbon atoms, preferably ethanol or isopropanol, or a water-alcohol mixture. The compositions can take the form of a lotion, emulsion gel, mousse or aerosol.

When the carrier is a water-alcohol mixture, the alcohol is present in an amount of between 10 to 70% by weight of the total weight of the composition. The pH of the aqueous compositions are generally between 3 and 10, and preferably between 5 to 7.

The compositions of the present invention may, if necessary, contain the dry extract of yarrow (*Achillea millefolium* L), such as defined above, in mixture with other compounds known to correct the oily and unaesthetic appearance of oily hair.

The compositions of the present invention may if necessary, contain the dry extract of yarrow (*Achillea millefolium* L) as defined above, in mixture with other treatment agents to obtain a particular cosmetic effect.

Particularly advantageous results are obtained with a water-soluble polymer of the polyamide type and more particularly with poly β-alanine containing 50 to 100% of the units —[CH$_2$— CH$_2$—CONH]— and 0 to 50% of the units

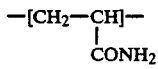

(see Belgian Patent No. 893,738).

The compositions of the present invention may take the form of shampoo, rinsing lotion, cream, shaping lotion such as setting lotions, brushing lotions, in the form of lacquers or in the form of products for treatment which can be applied before or after coloring or bleaching, before or after shampooing and before or after a permanent or a straightening.

When the compositions of the present invention take the form of shampoos, they also contain one or more surface-active agents. These surface-active agents can be anionic, non-ionic, cationic, amphoteric, or a mixture of the latter. The concentration of surface-active agents in the shampoos is usually between 3 and 50% by weight, preferably between 3 and 20%, and the pH is usually between 3 and 10.

When the compositions of the present invention take the form of rinsing lotions, they may be aqueous solutions or water-alcohol solutions, emulsions, thickened lotions or gels.

When the compositions take the form of emulsions, they can be non-ionic or anionic. The non-ionic emulsions principally consist of a mixture of oil and/or fatty alcohol and of polyethoxylated alcohol such as polyethoxylated stearyl or cetylstearyl alcohol. Cationic surface-active agents may be added to these compositions. Anionic emulsions are essentially constituted from soaps.

When the compositions take the form of thickened lotions or gels, they contain thickeners in the presence or absence of solvents. The thickeners that can be utilized are sodium alginate, gum arabic, xanthane gum, or cellulose derivatives such as methylcellulose, hydroxymethylcellulose, hydroxyethylcellulose, hydroxypropylcellulose, hydroxypropylmethylcellulose and carboxymethylcellulose. One can also obtain a thickening of the lotions by mixing polyethyleneglycol and polyethyleneglycol stearate or distearate or by a mixture of a phosphoric ester and amide. The concentration of thickener can vary from 0.5 to 30% by weight, typically 0.5 to 15% and preferably 0.5 to 5%. The pH of rinsing lotions varies essentially between 3 and 9, and preferably between 4.5 and 7.5.

When the compositions of the present invention take the form of combing lotions, shaping lotions, lotions referred to as setting lotions, brushing lotions or lacquers, these lotions generally include the dry extract of yarrow (*Achillea millefolium* L) in aqueous, alcoholic or water-alcohol solutions as well as with polymers, if necessary.

The polymers that may be utilized, include polyvinylpyrrolidone, copolymers of polyvinylpyrrolidone, vinyl acetate, copolymers of vinyl acetate, an unsaturated carboxylic acid such as crotonic acid, copolymers resulting from the polymerization of vinyl acetate, crotonic acid and an acrylic or methacrylic ester, copolymers resulting from the copolymerization of vinyl acetate and an alkylvinyl ether, and copolymers resulting from the copolymerization of vinyl acetate, crotonic acid and the vinylic ester of an acid with a long carbon chain, or of an allylic or methallylic ester of an acid with a long carbon chain, their concentration varying between 0.1 and 5% by weight with respect to the total weight of the compositions.

A specially preferred form of the hair composition of the present invention consists of a water-alcohol, no-rinse lotion containing 1 to 70% by weight of ethanol, and including 0.02 to 3% of dry extract of yarrow as defined above.

According to another specially preferred form, the hair composition consists of a water-alcohol, no-rinse lotion containing 1 to 70% by weight of ethanol and including 0.02 to 3% of the dry extract of yarrow as defined above and 0.01 to 3%, preferably 1% by weight of poly β-alanine.

These compositions can also be pressurized in aerosol. As a propellant one may use carbon dioxide, nitrogen, nitrous oxide, volatile hydrocarbons such as butane, isobutane, propane, and preferably chlorinated or fluorinated hydrocarbons.

The compositions of the present invention may also contain other ingredients typically utilized in cosmetic products such as scents, coloring agents, preserving agents, sequestering agents, thickening agents, softening agents, synergists and/or mousse stabilizers, solar filters, peptizing agents, fatty alcohols and waxes.

The invention will be better understood with the aid of the following examples which are not considered restrictive and in which, unless otherwise mentioned, the amounts and percentages are by weight.

Preparation of the Dry Extract of Yarrow (*Achillea millefolium* L) and Preparation of the Aqueous-Methanolic Extract An infusion is made by pouring one liter of deionized, boiling water on 150 g of previously pulverized flower tops of yarrow. After homogenization, the infusion is allowed to sit until it cools down, which takes about 3 hours. The infusion is then filtered on sintered glass under vacuum, yielding 680 ml of a brown aqueous solution. The solid residue of the filtration is then mixed with 300 ml of methanol. After stirring, the residue is filtered out and then washed twice with 100 and 200 ml of methanol, respectively. 580 ml of a turbid methanolic solution (colloidal precipitate) of brown-greenish color is thereby obtained. The aqueous and methanolic solutions are then mixed.

Oxidizing Treatment 630 ml of the water-methanol solution from above are then treated with 100 ml of sodium hypochlorite, with a 10° to 13° chlorometric titer containing about 3.5% of active chlorine.

An agglomeration and the formation of a precipitate become noticeable, while the supernatant solution does not become discolored. The addition of sodium hypochlorite continues until the color changes to orange, which requires the supplementary addition of 530 ml of sodium hypochlorite.

The solution is then allowed to sit for 24 hours at room temperature. During the 24 hour period a precipitate settles and a brownish color of the supernatant solution remains. After 24 hours, the mixture is filtered on paper and the clear solution with a brownish color is then completely evaporated under reduced pressure in a rotary evaporator. 57.75 g of "oxidized" dry extract of yarrow is thereby obtained.

The "oxidized" dry extract has the following characteristics:

| | |
|---|---|
| absorbance at 450 nm (aqueous solution, 0.2%) | 0.06 |
| sulfate ashes (g/%) | 94 |
| total N (g/%) | 0.5 |
| total sugars (g/%) | 3.5 |
| free glucose plus fructose (g/%) | 0.9 |
| polyphenolic derivatives (g/%) | 0.2 |
| formic acid (g/%) | ≈3.3 |
| acetic acid (g/%) | ≈5 |
| glycolic acid (g/%) | ≈1 |

For comparison, the dry extract of yarrow obtained above after complete evaporation of the water-methanol solution shows the following characteristics:

| | |
|---|---|
| absorbance at 450 nm (aqueous solution, 0.2%) | 0.27 |
| sulfate ashes (g/%) | 23 |
| total N (g/%) | 2.4 |
| total sugars (g/%) | 16 |
| free glucose plus fructose (g/%) | 3.8 |
| polyphenolic derivatives (g/%) | 5 |
| formic acid (g/%) | ≈0.35 |
| acetic acid (g/%) | ≈0.2 |
| glycolic acid (g/%) | <0.2 |

EXAMPLE 1

A no-rinse shaping lotion for oily hair is prepared with the following ingredients and conditions;

| | |
|---|---|
| copolymer polyvinylpyrrolidone-vinyl acetate (60/40%) | 0.2 g |
| ethanol | 45 g |
| "oxidized" dry extract of Achillea millefolium L | 2 g |
| preservative | 0.2 g |
| coloring agent | 0.2 g |
| pH = 6 | |
| water, sufficient amount for | 100 g |

EXAMPLE 2

A no-rinse hair lotion for oily hair is prepared with the following ingredients and conditions:

| | |
|---|---|
| "oxidized" dry extract of Achillea millefolium L | 1 g |
| poly β-alanine | 0.5 g |
| ethanol | 45 g |
| coloring agent | 0.2 g |
| preservative | 0.2 g |
| pH = 6 | |
| water, sufficient amount for | 100 g |

EXAMPLE 3

A rinsing gel for oily hair is prepared with the following ingredients and conditions:

| | |
|---|---|
| carboxymethylcellulose | 3 g |
| "oxidized" dry extract of Achillea millefolium L | 1.5 g |
| preservative | 0.3 g |
| coloring agent | 0.2 g |
| pH = 5 | |
| water, sufficient amount for | 100 g |

EXAMPLE 4

A shampoo for oily hair is prepared with the following ingredients and conditions:

| | |
|---|---|
| non-ionic surface-active agent according to example 1 of French Patent No. 71.17206 by condensation of 3.5 mols of glycidol on a $C_{11}$–$C_{14}$ α-diol | 10 g |
| "oxidized" dry extract of Achillea millefolium L | 5 g |
| preservative | 0.2 g |
| coloring agent | 0.2 g |
| pH = 5 | |
| water, sufficient amount for | 100 g |

EXAMPLE 5

A no-rinse lotion for oily hair is prepared with the following ingredients and conditions:

| | |
|---|---|
| "oxidized" dry extract of Achillea millefolium L | 0.05 g |
| poly β-alanine | 0.50 g |
| ethanol | 20 g |
| coloring agent | 0.3 g |
| preservative | 0.15 g |
| pH = 5.5 | |
| water, sufficient amount for | 100 g |

What is claimed is:

1. A process for the preparation of a non-allergenic dry extract of yarrow, comprising the steps of mixing flower tops of yarrow with water to produce an infusion, filtering said infusion to separate a solid residue from an aqueous extract, mixing said solid residue with methanol to produce a methanol solution, filtering said methanol solution and recovering a methanolic extract therefrom, mixing said aqueous extract and said methanolic extract to produce a water-methanol solution, oxidizing said water-methanol solution with sodium hypochlorite at room temperature and then after filtration recovering said dry extract of yarrow from the oxidized water-methanol solution by a technique selected from the group of techniques consisting of evaporation, atomization and freeze-drying.

* * * * *